United States Patent [19]
Mathys

[11] Patent Number: 5,674,244
[45] Date of Patent: Oct. 7, 1997

[54] LOCKING DEVICE ON A PLIERS-SHAPED TOOL

[75] Inventor: Robert Mathys, Bettlach, Switzerland

[73] Assignee: Synthes (U.S.A.), Paoli, Pa.

[21] Appl. No.: 641,207

[22] Filed: Apr. 30, 1996

Related U.S. Application Data

[63] Continuation of Ser. No. 208,037, Mar. 9, 1994, abandoned, which is a continuation of Ser. No. 975,584, filed as PCT/CH92/00118 Jun. 22, 1992, abandoned.

[30] Foreign Application Priority Data

Jul. 9, 1991 [CH] Switzerland ............... 02036/91

[51] Int. Cl.⁶ ............................................. A61B 17/28
[52] U.S. Cl. ........................................ 606/208; 81/338
[58] Field of Search .......................... 606/208; 81/338, 81/337, 336, 332, 331, 330, 329, 318, 319, 325

[56] References Cited

U.S. PATENT DOCUMENTS

| | | | |
|---|---|---|---|
| 1,944,116 | 1/1934 | Stratman | 81/49 |
| 2,881,649 | 4/1959 | Ball et al. | |
| 4,538,485 | 9/1985 | Saila | 81/336 |
| 4,896,661 | 1/1990 | Bogert et al. | 606/208 X |

FOREIGN PATENT DOCUMENTS

| | | |
|---|---|---|
| 827927 | 1/1952 | Germany . |
| 49-22760 | 8/1970 | Japan . |

*Primary Examiner*—Michael H. Thaler
*Attorney, Agent, or Firm*—Fish & Richardson, P.C.

[57] ABSTRACT

The locking device for a pliers-shaped tool, preferably a pair of pliers (1), has a lever (7) with a spring (8a) on the inner side of one handle and a shaped rod (9) on the inner side of the other handle (4b).

The shaped rod (9) has a catching element (10) and passes through an opening (14) in the lever (7). The lever has a sharp projection (15) in its opening (14), which engages the catching element (10) of the shaped rod (9) in the closed setting in such a way that the pliers (1) can only be closed. With these pliers (1), objects (5) can be gripped, held tight and let loose again. The locking device is entirely between the handles (4a and 4b) of the pliers (1). The pliers (1) with the locking devices can be used generally, but their primary application is in surgery.

16 Claims, 3 Drawing Sheets

LOCKING DEVICE ON A PLIERS-SHAPED TOOL

This is a continuation of application Ser. No. 08/208,037 filed on Mar. 9, 1994 now abandoned, which is a continuation of Ser. No. 07/975,584, filed as PCT/CH92/00118 Jun. 22, 1992, now abandoned.

FIELD OF THE INVENTION

The invention involves a locking device for a pliers-shaped tool, which functions to secure the tool onto an object, to keep it secured, and to loosen it.

BACKGROUND

A pliers-shaped tool consists of two handles which are movable against each other about a pivot point. On one side of the pivot point, the handles, each having an extension, form jaws. On the other side, each handle forms a grip, in some cases with finger holes. The invention will be explained as applied to pliers which are the most common pliers-shaped tool.

Locking devices for pliers-shaped tools are already well known.

Pliers exist in which a movable long screw is positioned in a handle and passes through a hole in the other handle. A nut on the outer side of the other handle is threaded onto the screw after the jaw of the pliers has gripped an object, so that the object is firmly held by the jaws of the pliers. The object is freed when the nut is sufficiently loosened. This contrivance is applicable even if the pliers is designed to be very rigid, owing to the continuous threading capacity of the nut for any given diameter of the object within the jaw width of the pliers. However, it requires two hands for operation. The screw projects beyond the handle; thus, the applicability of such pliers where space is limited as, for example, in surgery, is restricted.

Another type of pliers has strips that move against each other on the inner side of each of the handles. These strips move past each other in close proximity. On the sides that face each other, the strips have numerous triangular-shaped projections, so that the handles are able to be locked by hooking the triangular projections on the strips at various distances from each other. With pliers made to be pliable and elastic, for example pliers with long handles, all objects that are within the maximum jaw width of the pliers can be gripped tightly, with the gripping pressure differing according to the position of the handles. Letting the object go using one hand is possible only if the handles have finger holes at the ends like scissors. In letting the object go from the pliers, the release of the handle transverse to the direction of opening necessitates a certain physiologically unnatural expenditure of energy.

Yet another locking device for a pliers is described in WO89/06939. In this type of pliers, one of the handles has a toothed rack on its inner side between the pivot point and the grip. The rack extends through an opening in the second handle. At this opening there is a safety catch which acts on the toothed rack by means of three different settings. In its first setting, the pliers can only be closed. In the second setting, the pliers can only be opened. In the third setting, the pliers can be either closed or opened in an unimpeded manner.

In the first setting, the pliers grip an object as long as their jaw is adjusted to the object's diameter. They let the object go if another setting is made. The settings are made on a switching mechanism coaxial with the safety catch. They are held upright by a ball located on a compression spring which at any given time engages one of the three settings in the safety catch. These pliers can be operated one-handed. However, they require the toothed rack to extend through the second handle externally of the pliers, thus taking up a large amount of space like the first set of pliers with the screw, mentioned above.

SUMMARY OF THE INVENTION

The present invention is intended to provide a pliers-shaped tool having a locking device that is located within the tool, but can nonetheless be operated simply and safely using only one hand.

According to the invention this objection is achieved by providing, in a pliers-shaped tool having jaws, a first handle and a second handle, a locking device comprising a gripping mechanism movable to different settings, on said first handle, and a shaped rod having a catching device, on the inner side of said second handle, said gripping mechanism comprising a lever, the lever and the shaped rod being positioned between the two handles, said lever having an opening to receive the shaped rod, said lever being configured to assume an open setting position and a closed setting position and having a sharp projection associated with said opening to engage the catching device when said lever is in its closed setting position, thus permitting the tool only to be closed, the lever having surfaces between which the shaped rod can move freely when the lever is in the open setting position so that the tool can be opened as well as closed.

BRIEF DESCRIPTION OF THE DRAWINGS

The invention will be further described in connection with the appended drawings in which:

FIG. 1aa is an enlarged view of the lever portion of the locking device of FIG. 1a.

FIG. 1bb is an enlarged view of the lever portion of the locking device of FIG. 1b.

DETAILED DESCRIPTION OF SPECIFIC EMBODIMENTS

Figure 1A:
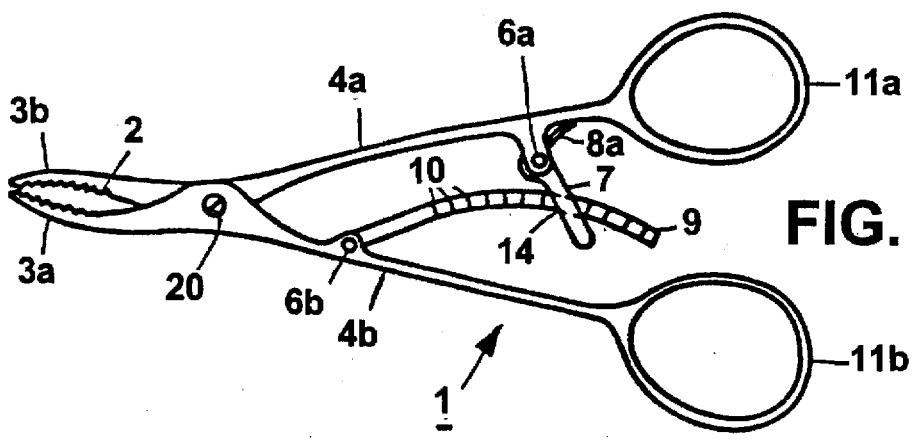
FIG. 1a is a view in side elevation of a pair of pliers according to the invention with a locking device in an open setting.
Figure 1A:
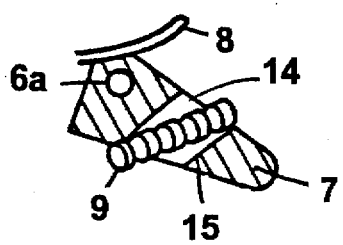
Figure 1B:
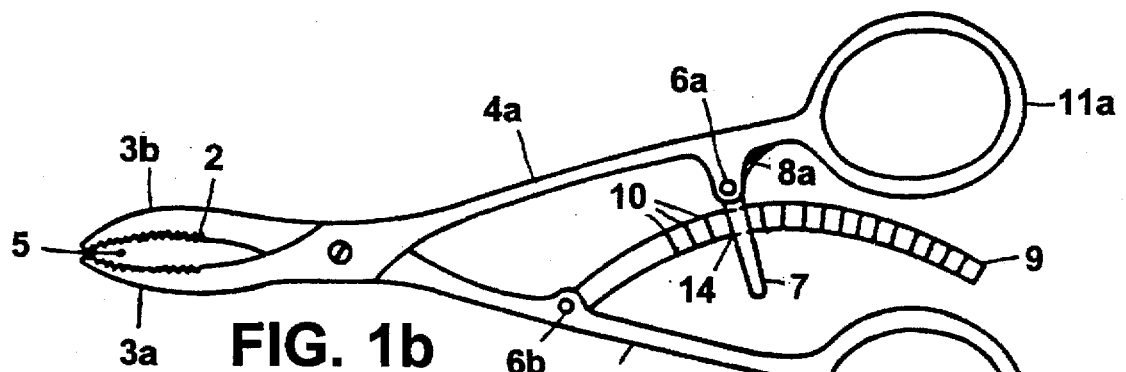
FIG. 1b is a view in side elevation of the pliers of FIG. 1a and 1aa.
Figure 1B:

Referring to FIG. 1a, there is shown a pair of pliers 1 according to the invention in a setting (open setting) in which their handles 4a and 4b are freely movable about the pivot point 20. FIG. 1b shows the same pliers in a setting (closed setting) in which their handles 4a and 4b can only be closed.

The pliers 1 have jaws 2, whose sections 3a and 3b have teeth. The pliers also have two handles 4a and 4b, both ending in finger holes 11a and 11b on the gripping end. To use the pliers 1, one must put the thumb and middle finger through each finger hole 11a and 11b, and operate a lever 7 (to be described later) using the index finger. In FIG. 1b, which shows the pliers 1 in the closed position, an object 5 is indicated as embraced by jaws 2.

On the inner side of the second handle 4b, a shaped rod 9 is swivel-mounted by means of a pin 6b. On the rod 9 is a catching element 10, shown as an array of periodically arranged segments which will be described in more detail below. In addition the pliers have the lever 7 attached to the inner side of the first handle 4a by a pin 6a. This lever 7 is shown in more detail in both FIGS. 1aa and 1bb.

The lever 7 and the shaped rod 9 are entirely situated between the handles 4a, 4b and do not project outwardly beyond them at any point. The lever 7 has an opening 14 through which the shaped rod 9 runs. The lever 7 is configured so that it can assume only two stable settings, an open setting and a closed setting. In the embodiment shown in FIGS. 1–4, this is achieved by having the end of the lever that faces the handle 4a formed in an angled configuration adjoining a flat piece of a leaf spring 8a. In all intermediate settings, the lever is brought back by the spring 8a to the open setting or the closed setting.

At its opening 14, the lever 7 has a sharp projection 15 which it engages the catching element 10 of the shaped rod 9. This engagement takes place in such a way that the pliers 1 can only be closed. To achieve this, the shaped rod 9 is configured so that the lever 7 and the side of projection 15 that faces the gripping end of the handles is perpendicular or nearly perpendicular to the shaped rod 9 in the closed position.

The segments of the catching element 10 of the shaped rod 9 likewise have an edge that runs perpendicularly to the direction of the shaped rod 9, and are always pointed toward the grip end of the handles 4a and 4b. Behind the perpendicular edges the sharp projection 15 of the lever 7 catches hold, and by this means the lever 7 can no longer be displaced toward the grip end of the handles 4a and 4b. If an object 5 is in the jaws of the pliers 1, then it is gripped tight as soon as the jaws 2 have closed over the object, and is automatically held fast by the pliers 1.

In the open setting, the shaped rod 9 lies on a broad surface. It can then run freely through the opening 14, and the pliers 1 can be opened and closed without restriction. An object 5 which is held fast in the jaws 2 of the pliers 1 can be let go when the lever 7 is brought into the open position by the operator's finger.

Figure 2:
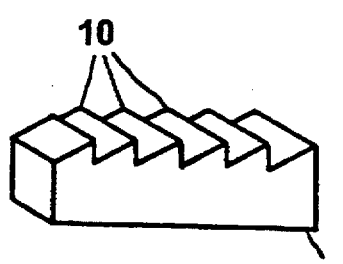
FIG. 2 is a perspective view of a catching device for use in a tool according to the invention in the form of a shaped rod having a rectangular cross section and a toothed rack.
Figure 3:
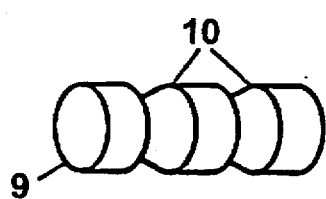
FIG. 3 is a perspective view of a catching device for use in a tool according to the invention in the form of a shaped rod having a circular cross section and turned grooves.

Some examples of the configuration of the catching element 10 of the shaped rod 9 are shown in FIG. 2, in which a rectangular shaped rod 9 is furnished with a toothed rack, and in FIG. 3, where the shaped rod 9 has a circular cross section and is provided with turned incisions in the form of ring grooves. The shaped rod can also be configured to have a screw thread or other suitable forms. In all cases the shapes of the catching element 10 are configured asymmetrically, with an edge running perpendicular to the direction of the shaped rod 9, and arrayed in the direction of the handle grips.

Figure 4A:
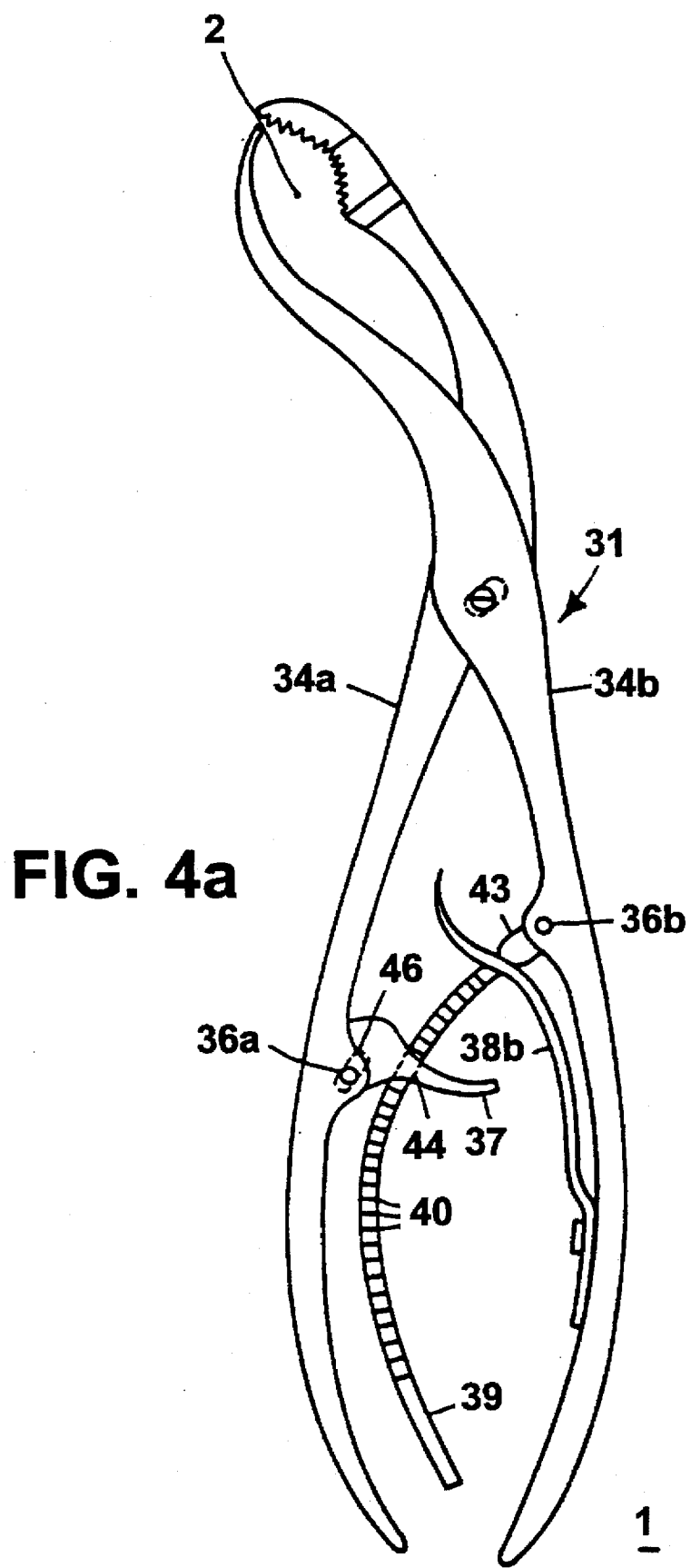
FIG. 4a is a view in side elevation of a second embodiment of pliers according to the invention with another locking device in the closed position.
Figure 4B:
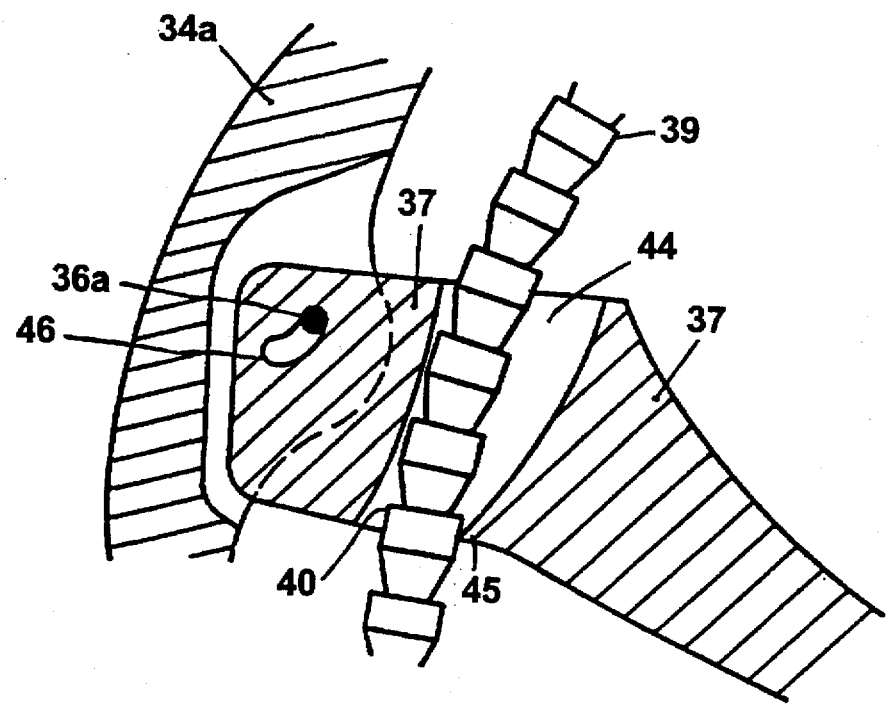
FIG. 4b is a schematic enlarged view, partly in vertical section, of the lever of the tool of FIG. 4a in the open position.
Figure 4C:
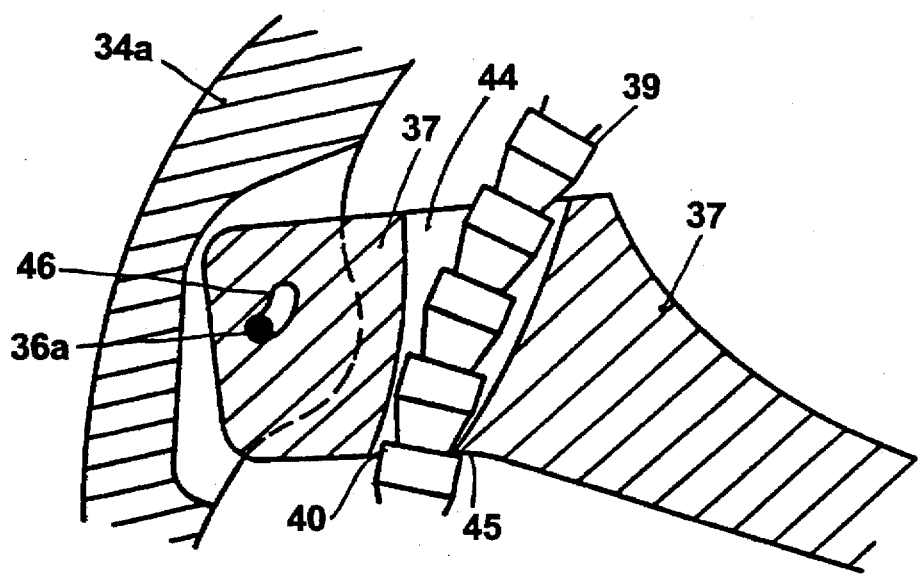
FIG. 4c is a schematic view of the lever of FIG. 4b in the closed position.

FIG. 4a shows another embodiment of pliers 31 according to the invention in a closed setting. FIG. 4b shows the section around its lever 37 in the open setting. FIG. 4c shows the section around its lever in the closed setting. FIGS. 4a–c will be discussed together.

In the open setting of the lever 37, the shaped rod 39 moves without restriction in the opening 44 of the lever 37, and the pliers 31 can be opened and closed. The shaped rod 39 is flexibly attached to the first handle 34a of the pliers 31 by means of the lever 37. It does so with the help of a suitably shaped spring 38b (in this case, S-shaped), guided by a sliding pad 43. Thus the pliers 31 tend to open to the maximum extent possible and can only be closed by pressing the handles 34a and 34b toward each other.

Because of the spring 38b which forces the pliers 31 to open, the locking device can be designed differently from that described above. The lever 37 has a crescent-shaped slot 46 in which the pin 36a that connects the lever 37 with the first handle 34a. Here also, the lever 37 may assume two stable settings. In the open setting, the pin 36a is seated in the section of the slot 46 which is closer to the jaws as shown in FIG. 4b. Owing to the tension which the spring 38 exerts on the shaped rod 39, the latter is pushed toward the side of the opening 44 in the lever 37 that faces the first handle 34a, and runs freely on a broad surface of the opening 44.

If one places the lever 37 in the closed setting, the pin 36a moves to the section of the slot hole 46 that is closer to the grip end, and the lever 37 stands nearly perpendicularly to the shaped rod 39. The sharp projection 45 in the opening 44 of the lever 37 can now engage the catching element 40 of the shaped rod 39 and permits the pliers 31 only to close. The lever 37 is thus capable of assuming only two stable settings, the closed setting and the open setting. The remaining parts of the pliers 31 perform the same functions as in the embodiment of FIGS. 1a and 1b.

Pliers according to the invention thus automatically grip an object in their jaws, if in the closed setting they have been closed to a sufficient extent that the object is gripped by the jaws. They can let it loose again if the lever is shifted to the open position by the operator's finger.

With a locking device according to the invention, of which examples are shown in the drawings, the levers 7, 37 have openings 14, 44 through which a shaped rod such as 9, 39, runs. The rod has a catching element. The lever and the shaped rod are positioned so as to be entirely between the handles of the tool. The lever is configured in such a way that, owing to spring pressure, it can assume only two stable settings, an open setting and a closed setting. Associated with the opening, the lever has a projection with which, in the closed setting, it engages the catching element of the shaped rod, so that the pliers can only be closed. In contrast, in the open setting, the shaped rod moves over the broad surface of the opening of the lever, so that the pliers can be freely opened and closed.

The locking device according to the invention can also be used with pliers in which, for example, the jaw width and the shape of the jaws can be varied using a slotted hole at the pivot point between the two handles (so-called self-centering pliers).

Locking devices according to the invention can be created as kits for retrofitting pliers-shaped tools.

The locking device according to the invention achieves the stated intention, since it makes possible one-handed operation of a pliers-shaped tool, and is configured to be entirely between the handles of the tool. Tools equipped with it can be used generally in industry and by domestic users, but above all they are useful in surgery.

I claim:

1. In a pliers-shaped tool having jaws, a first handle having a first end connected to a first jaw and a second end remote from said first jaw, a second handle having a first end connected to a second jaw and a second end remote from said second jaw, a locking device positioned completely between said handles and extending longitudinally of said handles to a point which is nearer to said jaws than are the second ends of said handles, said locking device, in its entirety, being positioned nearer to the jaws than are the second ends of said handles and further comprising a gripping mechanism, movable to different settings, on said first handle, and a shaped rod having a catching device on the inner side of the second handle, said gripping mechanism comprising a flat spring adjacent said first handle, and a lever having an angled side with two adjoining plates facing the first handle, said lever being positioned so that in an open setting position one of said surfaces abuts said spring and in a closed setting position the other surface abuts said spring whereby said spring acts to bring the lever back to said open or closed setting position from other positions, the lever and the shaped rod being positioned between the two handles, said lever further having a through hole to receive the shaped rod, and a sharp projection associated with said through hole to engage the catching device when said lever is in its closed setting position, thus permitting the pliers only to be closed, the through hole having surfaces between which the shaped rod can move freely when the lever is in the open setting position so that the pliers can be opened as well as closed.

2. In a pliers-shaped tool having jaws, a first handle having a first end connected to a first jaw and a second end remote from said first jaw, a second handle having a first end connected to a second jaw and a second end remote from said second jaw, a locking device positioned completely between said handles and extending longitudinally of said handles to a point which is nearer to said jaws than are the second ends of said handles, said locking device, in its entirety, being positioned nearer to the jaws than are the second ends of said handles and further comprising a gripping mechanism movable to different settings on said first handle, and a shaped rod having a catching device on the inner side of the second handle, said gripping mechanism comprising a lever, the lever and the shaped rod being positioned between the two handles, said lever having a through hole to receive the shaped rod, said lever being configured to assume an open setting position and a closed setting position and having a sharp projection associated with said through hole to engage the catching device when said lever is in its closed setting position, thus permitting the pliers only to be closed, the through hole having surfaces between which the shaped rod can move freely when the lever is in the open setting position so that the pliers can be opened as well as closed, said locking device further comprising an S-shaped spring on said second handle urging said tool toward an open position, said spring having an aperture to accommodate the shaped rod.

3. The locking device claimed in claim 2 and comprising means pivotally attaching said shaped rod to the second handle, said rod extending through the aperture in said spring and the through hole in said lever and said spring being shaped to press the lever against the first handle through the rod.

4. The locking device according to claim 3 and comprising a sliding pad, said spring acting on the shaped rod by means of said sliding pad.

5. In a pliers-shaped tool having jaws, a first handle having a first end connected to a first jaw and a second end remote from said first jaw, a second handle having a first end connected to a second jaw and a second end remote from said second jaw, a locking device positioned completely between said handles and extending longitudinally of said handles to a point which is nearer to said jaws than are the second ends of said handles, said locking device, in its entirety, being positioned nearer to the jaws than are the second ends of said handles and further comprising a gripping mechanism movable to different settings on said first handle, and a shaped rod having a catching device on the inner side of the second handle, said gripping mechanism comprising a lever, a crescent shaped slot in said lever, and a pin seated in said slot and connecting said lever to said first handle, the lever and the shaped rod being positioned between the two handles, said lever having a through hole to receive the shaped rod, said lever being configured to assume an open setting position in which said pin is seated at the end of said crescent shaped slot nearer to said jaws, and a closed setting position in which said pin is in a section of the slot more remote from the jaws and a sharp projection associated with said through hole to engage the catching device when said lever is in its closed setting position, thus permitting the pliers only to be closed, the through hole having surfaces between which the shaped rod can move freely when the lever is in the open setting position so that the pliers can be opened as well as closed, said locking device further comprising a spring on said second handle urging said tool toward an open position.

6. In a pliers-shaped tool having jaws and handles adapted to be held by a human hand, a first handle having a first end forming a first jaw and a second end remote from said first jaw, a second handle having a first end forming a second jaw and a second end remote from said second jaw, means pivotally attaching said handles to one another at a pivot point, a locking device positioned completely between said handles and extending longitudinally of said handles to a point which is nearer to said pivot point than are the second ends of said handles, said locking device, in its entirety, being positioned nearer to the jaws than are the second ends of said handles and further comprising a gripping mechanism movable to different settings on said first handle, and a shaped rod, having a catching device, on the second handle, said gripping mechanism comprising a lever, the lever and the shaped rod being positioned between the two handles, said lever having a through hole to receive the shaped rod, said lever being configured to assume an open setting position and a closed setting position and having a sharp projection associated with said through hole to engage the catching device when said lever is in its closed setting position, thus permitting the pliers only to be closed, the through hole having surfaces between which the shaped rod can move freely when the lever is in the open setting position so that the pliers can be opened as well as closed, said shaped rod being pivotally attached to the inner side of said second handle at a point nearer to said pivot point than to the second ends of said handles.

7. The locking device claimed in claim 6 and comprising a spring on said second handle, said spring urging said tool toward an open position.

8. The locking device according to claim 7, wherein said lever is shaped so that in the closed setting it is perpendicular to the shaped rod.

9. The locking device claimed in claim 8, wherein the catching device on the shaped rod has perpendicular surfaces facing the end of said handles remote from the jaws.

10. The locking device claimed in claim 7 and wherein said spring is S-shaped and comprises an aperture for accommodating the shaped rod.

11. The locking device claimed in claim 10 and comprising means pivotally attaching said shaped rod to the second handle, said rod extending through the aperture in said spring and the through hole in said lever and said spring being shaped to press the lever against the first handle through the rod.

12. The locking device according to claim 11 and comprising a sliding pad, said spring acting on the shaped rod by means of said sliding pad.

13. The locking device according to claim 6, wherein the shaped rod has a circular cross section, and the catching device comprises periodically placed ring grooves.

14. The locking device according to claim 6, wherein the shaped rod has a cross section with at least two edges, and the catching device comprises a toothed rack.

15. The locking device claimed in claim 6 and comprising a flat spring adjacent said first handle, said lever having an angled side with two adjoining planes facing the first handle, said lever being positioned so that in the open setting position one of said surfaces abuts said spring and in the closed setting position the other surface abuts said spring whereby said spring acts to bring the lever back to said open or closed setting position from other positions.

16. The locking device claimed in claim 6 wherein said lever and said rod are positioned so that said lever can be moved between said open and closed positions by a hand holding said handles.

* * * * *